(12) United States Patent
Moriwaki et al.

(10) Patent No.: US 9,291,551 B2
(45) Date of Patent: Mar. 22, 2016

(54) IMAGING APPARATUS AND IMAGING METHOD (71) Applicant: DAINIPPON SCREEN MFG. CO., LTD., Kyoto (JP)

(72) Inventors: Sanzo Moriwaki, Kyoto (JP); Hiroki Fujimoto, Kyoto (JP)

(73) Assignee: SCREEN Holdings Co., Ltd. (JP)

(*) Notice: Subject to any disclaimer, the term of this patent is extended or adjusted under 35 U.S.C. 154(b) by 76 days.

(21) Appl. No.: 14/314,603

(22) Filed: Jun. 25, 2014

(65) Prior Publication Data
US 2015/0064737 A1 Mar. 5, 2015

(30) Foreign Application Priority Data
Aug. 29, 2013 (JP) .................... 2013-177573

(51) Int. Cl.
G01N 21/25 (2006.01)
G01N 21/47 (2006.01)

(52) U.S. Cl.
CPC .............. G01N 21/255 (2013.01); G01N 21/47 (2013.01); G01N 2201/064 (2013.01); G01N 2201/0668 (2013.01)

(58) Field of Classification Search
None
See application file for complete search history.

(56) References Cited

U.S. PATENT DOCUMENTS

2013/0129181 A1   5/2013   Glensbjerg et al. ........... 382/133
2014/0287452 A1*  9/2014   Sugiyama ............ G02B 21/088
                                                          435/29

FOREIGN PATENT DOCUMENTS

| JP | 2005-300439 | 10/2005 |
| JP | 2006-098198 | 4/2006 |
| JP | 2013-072684 | 4/2013 |

OTHER PUBLICATIONS

Office Action issued on Feb. 17, 2015 in corresponding Japanese Patent Application No. 2013-177573.

* cited by examiner

Primary Examiner — Dave Czekaj
Assistant Examiner — Nam Pham
(74) Attorney, Agent, or Firm — Ostrolenk Faber LLP (57) ABSTRACT An imaging apparatus for imaging a two-dimensional image of an imaging object comprises a holder which holds a sample container carrying a biological sample as the imaging object on a carrying surface, a light emitting part which emits light toward the carrying surface, an imager which includes a strip-like light receiving part, receives the light incident on the light receiving part and thereby images an image of a strip-like region of the carrying surface, a strip-like light shield which shields a part of light emitted from the illuminator toward the strip-like region, and a mover which integrally and relatively moves the light emitting part, the light receiving part and the light shield with respect to the sample container.

9 Claims, 9 Drawing Sheets

IMAGING APPARATUS AND IMAGING METHOD

CROSS REFERENCE TO RELATED APPLICATION

The disclosure of Japanese Patent Application No. 2013-177573 filed on Aug. 29, 2013 including specification, drawings and claims is incorporated herein by reference in its entirety.

BACKGROUND OF THE INVENTION

1. Field of the Invention

This invention relates to an imaging apparatus and an imaging method for imaging a biological sample carried in a sample container.

2. Description of the Related Art

In medical or bio-scientific experiments, biological samples such as specimen tissues extracted from biological bodies or cells cultured in liquids or gel-like media are observed and measured. Conventionally, it has been a general practice to stain a biological sample with an appropriate dye matching an imaging purpose and image the biological sample with enhanced visibility. However, to avoid damage to a sample, the sample needs to be imaged without being stained in some cases. A configuration example of an imaging apparatus for such a purpose is disclosed in JP2013-072684A. In the imaging apparatus disclosed in this literature, illumination light is incident on a sample such as cells cultured in a recess (well) formed in a microplate from a light source arranged above the sample. The light transmitted downward through the sample is received by a line sensor and thus a two-dimensional image of the sample is imaged by the scanning of the line sensor.

The apparatus disclosed in the above literature is suitable for imaging a thick imaging object such as a cell cluster three-dimensionally cultured in a relatively deep well. On the other hand, in imaging, for example, cells or the like cultured by adhesion culture on an inner bottom surface of a container as an imaging object, a good image may not be obtained. This is because light incident on the cells or the like mostly transmits to reduce a change in the quantity of the transmitted light caused by the presence or absence of the cells or the like and it is difficult to obtain a high image contrast since the sample is thin.

To solve this problem, it is considered to increase or decrease a light quantity of illumination light by a diaphragm and apply a dark field imaging technology. However, in these cases, it may become difficult to observe the structure and the like of an imaging object due to insufficient brightness of an image. Thus, it is desired to establish an imaging technology capable of providing a good image contrast by a simple method even if an imaging object is relatively thin.

SUMMARY OF THE INVENTION

This invention was developed in view of the above problems and aims to provide a technology capable of providing a good image contrast and performing imaging by a simple configuration even if an imaging object is a relatively thin biological sample.

An aspect of the present invention is an imaging apparatus for imaging a two-dimensional image of an imaging object. The imaging apparatus comprises: a holder which holds a sample container carrying a biological sample as the imaging object on a carrying surface; an illuminator which emits light from a light emitting part facing the carrying surface of the sample container held by the holder toward the carrying surface; an imager which includes a strip-like light receiving part provided at a side of the carrying surface opposite to the light emitting part and along a first direction parallel to the carrying surface, receives the light incident on the light receiving part and images an image of a strip-like region along the first direction out of the carrying surface; a strip-like light shield which extends in a direction parallel to the first direction between the light emitting part and the carrying surface and shields a part of light emitted from the light emitting part toward the strip-like region; and a mover which integrally and relatively moves the light emitting part, the light receiving part and the light shield in a second direction parallel to the carrying surface and intersecting with the first direction with respect to the sample container held by the holder.

Another aspect of the present invention is an imaging method. The imaging method comprises: a first step of arranging a light emitting part to face a carrying surface of a sample container carrying a biological sample as an imaging object on the carrying surface, arranging a light shield configured to shield a part of light emitted from the light emitting part and propagating toward the carrying surface between the light emitting part and the carrying surface, and arranging a light receiving part of an imager configured to image an image of a strip-like region along a first direction parallel to the carrying surface out of the carrying surface at a side of the carrying surface opposite to the light emitting part; and a second step of imaging a two-dimensional image of the imaging object by integrally and relatively moving the light emitting part, the light receiving part and the light shield in a second direction intersecting with the first direction with respect to the sample container, wherein the light shield is a strip-like member which extends in the first direction between the light emitting part and the carrying surface.

In the invention thus configured, illumination light to be incident on the imaging object from the light emitting part is partly shielded by the light shield extending in the first direction which is a longitudinal direction of a strip-like image imaged by the imager. In imaging a two-dimensional image by moving the light receiving part of the imager relative to the imaging object to scan the imaging object, the light emitting part and the light shield also move integrally with the light receiving part relative to the imaging object.

In such a configuration, the strip-like light shield crosses the light emitting part to shield a part of the light emitting part when the light emitting part is viewed from the strip-like region of the carrying surface. Conversely, if the imaging object is viewed from the light emitting part side, a shadow of the light shield is cast on the imaging object. An extending direction of the shadow is the same as that of a one-dimensional image imaged by the imager. According to the knowledge of the inventors of the present invention, an image of the imaging object imaged at a side opposite to the light emitting part under such an illumination condition includes transmitted light components and scattered light components. The transmitted light components are bright but have a low image contrast due to transmitted light transmitted from the light emitting part and received through the imaging object. The scattered light components are incident on the light receiving part by the illumination light from such a direction as not to be directly incident on the light receiving part being scattered in the imaging object. The scattered light components have a small light quantity, but strongly reflect optical characteristics of the imaging object. Thus, an image in which these light components are mixed has both the brightness of the image and an image contrast. By setting the illumination condition in such a manner that those are mixed at an appropriate ratio, more excellent image quality can be obtained.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

First Embodiment

Figure 1:
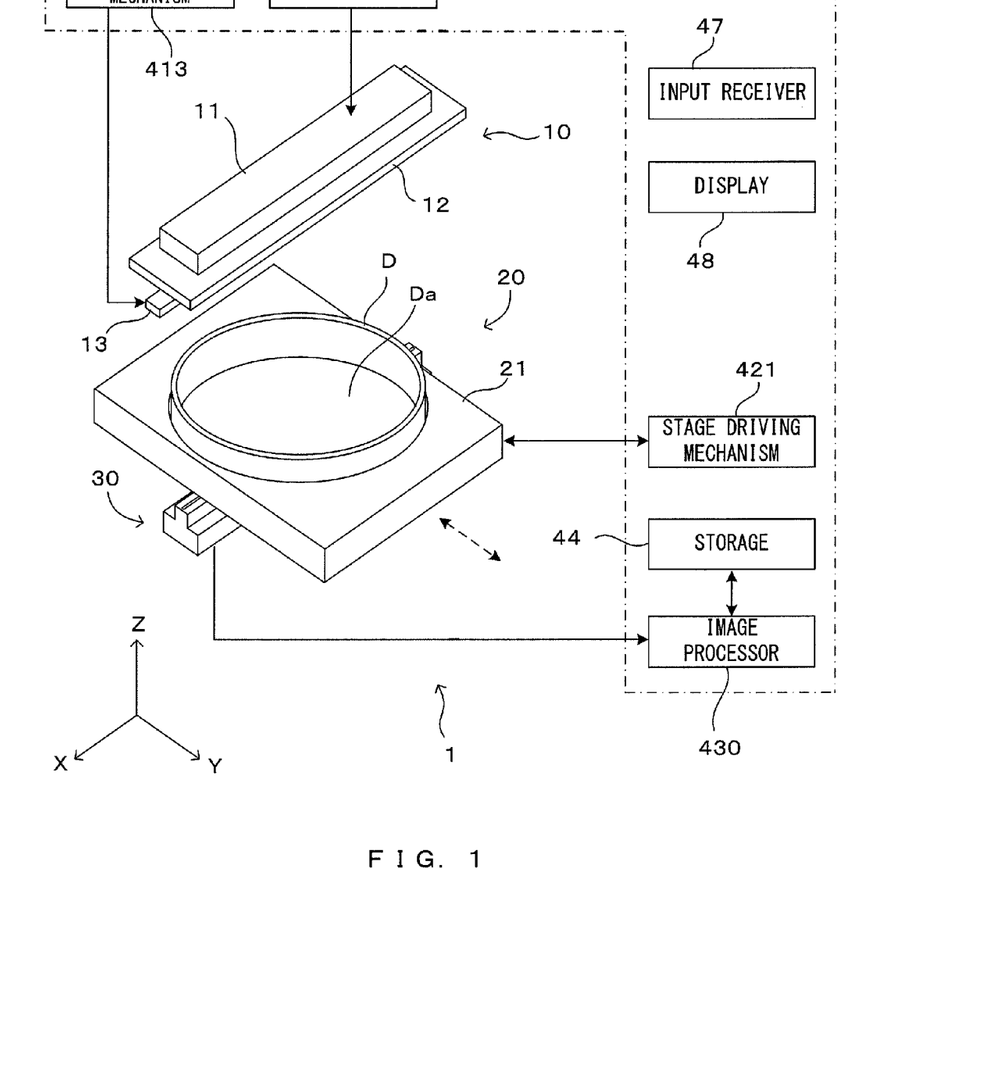
FIG. 1 is a view showing a main configuration of a first embodiment of an imaging apparatus according to the invention.
Figure 2:
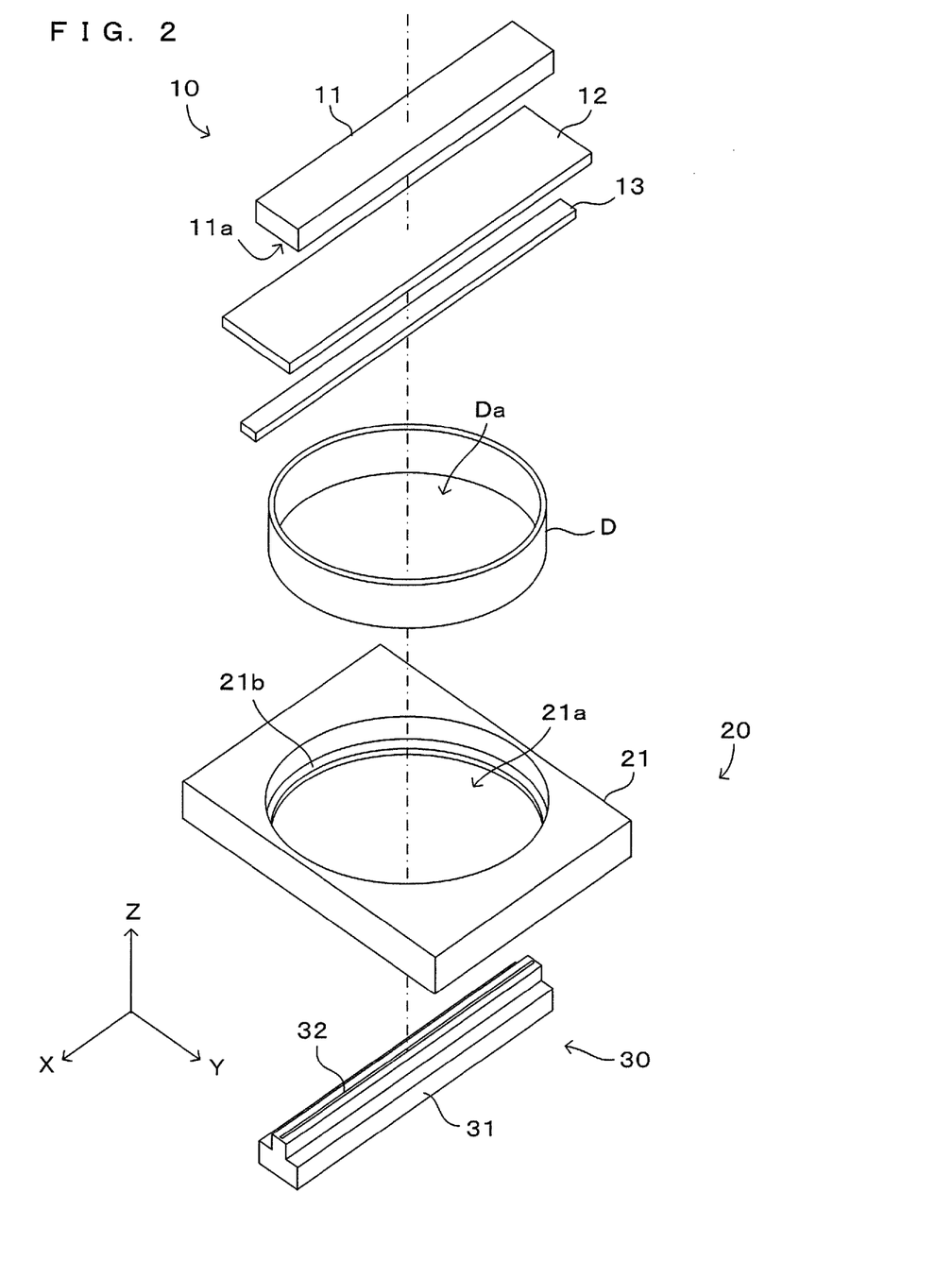
FIG. 2 is an exploded perspective view of the imaging apparatus of FIG. 1.

FIG. 1 is a view showing a main configuration of a first embodiment of an imaging apparatus according to this invention. FIG. 2 is an exploded perspective view of the imaging apparatus of FIG. 1. An XYZ orthogonal coordinate system is set as shown in FIG. 1 for the following description. Here, an XY plane represents a horizontal plane and a Z axis represents a vertical axis.

This imaging apparatus 1 includes a holding unit 20 for holding a shallow cell culture dish (hereinafter, referred to merely as "dish") D for carrying a biological sample as an imaging object substantially in a horizontal posture. An illumination unit 10 for illuminating the sample and an imaging unit 30 are respectively arranged above and below the holding unit 20, and a control unit 40 is provided to control the operation of each of these units. In FIG. 1, a supporting mechanism, a housing and the like for fixing each unit are not shown to clearly show the internal structure of the apparatus.

As shown in FIGS. 1 and 2, the illumination unit 10 includes a light source 11 for emitting light downward, a diffusion plate 12 arranged below the light source 11 to diffuse light emitted from a light emitting surface 11a of the light source 11, and a light shielding member 13 arranged below the diffusion plate 12. The light source 11 has a substantially rectangular plate shape extending in an X direction, and a plurality of white LEDs are, for example, provided as light emitting elements for emitting white light on the lower surface of the light source 11. Specifically, the lower surface of the light source 11 serves as the light emitting surface 11a and white light is emitted downward as illumination light from the light emitting surface 11a. The turning on and off and an emission light quantity of the light source 11 are controlled by a light source control unit 411 provided in the control unit 40.

The diffusion plate 12 is a substantially rectangular plate-like member having a plane size larger than the light emitting surface 11a of the light source 11 and extending in the X direction, and formed, for example, by a milky white resin plate or glass plate. A light quantity distribution of light emitted from the light source 11 is uniformized by the diffusion plate 12. The light shielding member 13 is an opaque strip-like member formed by a flat plate short in a Y direction and long in the X direction, and arranged to block a part of an optical path of illumination light emitted downward from the light source 11 via the diffusion plate 12. In this way, the light emitted from the light source 11 is partly shielded. To suppress light reflection on a surface, the light shielding member 13 is desirably formed of a black material or a surface thereof is colored in black.

Note that the light shielding member 13 of the illumination unit 10 is supported movably in the Y direction and moves between a light shielding position where illumination light is partly shielded at a position directly below the diffusion plate 12 shown in FIG. 1 and a retracted position (see FIG. 4B) which is retracted in the Y direction from the position below the diffusion plate 12 and where the illumination light is not shielded. A light shielding member driving mechanism 413 provided in the control unit 40 moves the light shielding member 13.

The holding unit 20 is arranged below the illumination unit 10 configured as described above. The holding unit 20 includes a stage 21 with an opening in conformity with external dimensions of the dish D having a circular bottom surface. More specifically, the stage 21 is a flat member provided with an opening 21a having a diameter slightly larger than an outer diameter of the dish D in a central part. An inner wall surface of the opening 21a projects inwardly to form a projection 21b near the bottom surface of the stage 21. When the dish D is set on the stage 21, an outer peripheral part of the bottom surface of the dish D is held by the projection 21b. Thus, a central part of the bottom surface of the dish D is uncovered in this state. The stage 21 is coupled to a stage driving mechanism 421 of the control unit 40, and the stage driving mechanism 421 moves the stage 21 horizontally in the Y direction.

The dish D is formed of a transparent material such as glass, polystyrene or polycarbonate. The dish D typically has, for example, a diameter of several tens of mm, a height of a peripheral edge part of between ten and twenty mm and a thickness of the bottom surface of about 1 mm, but there is no limitation to these numerical values. In the dish D used in this embodiment, an inner bottom surface Da thereof serves as a flat culture surface. Biological samples such as cells, bacteria and microorganisms seeded and cultured together with a predetermined amount of a predetermined type of a medium are prepared on the culture surface in advance. These biological samples are an imaging object of this imaging apparatus 1. For example, cell tissues and the like cultured by adhesion culture on the dish inner bottom surface can be an imaging subject.

When the dish D is held on the stage 21 and the stage 21 is positioned below the illumination unit 10 by the stage driving mechanism 421, the illumination unit 10 faces the dish D. The dish D is moved in the Y direction together with the stage 21 by the stage driving mechanism 421, whereby the illumination unit 10 relatively moves with respect to the dish D.

The imaging unit 30 is arranged below the holding unit 20. Although described in detail later, the imaging unit 30 includes a housing 31 extending in the X direction and a light receiving window 32 provided on the upper surface of the housing 31, having a function of receiving light incident from above and long and narrow in the X direction. This imaging unit 30 images a one-dimensional image in the X direction by outputting an electrical signal corresponding to the quantity of light incident on the light receiving window 32 for each position in the X direction. Light emerging from the bottom surface of the dish D held on the stage 21 can be incident on the light receiving window 32 to image a one-dimensional image of an imaging object (biological sample) in the X direction viewed from a bottom surface side of the dish D. Further, by repeatedly performing imaging of the one-dimensional image while the dish D is moved in the Y direction by the stage driving mechanism 421, a two-dimensional image of the imaging object can be imaged. Specifically, in this apparatus, a two-dimensional image is imaged with the X direction as a main scanning direction and the Y direction as a sub scanning direction.

When the stage 21 is horizontally moved by the actuation of the stage driving mechanism 421, the illumination unit 10 and the imaging unit 30 are stationary. Accordingly, only the dish D held on the stage 21 moves relative to these. Relatively, the illumination unit 10 (light source 11, diffusion plate 12, light shielding member 13) and the imaging unit 30 are integrally moved to scan in the horizontal direction (Y direction) with respect to the stage 21 and the dish D.

An electrical signal output from the imaging unit 30 and corresponding to an image of an imaging object is converted into a digital signal (image data) by an unillustrated AD converter and input to an image processor 430 of the control unit 40. The image processor 430 applies various processings to the obtained image data.

The control unit 40 further includes a storage 44 such as an image memory for storing image data. The storage 44 stores image data corresponding to images imaged by the imaging unit 30, and various processed image data and intermediate data thereof generated by the image processor 430.

Besides the above, the control unit 40 includes an input receiver 47 for receiving an operation input given from a user or an external apparatus on the operation of the apparatus and the setting of control parameters, and a display 48 for displaying operating conditions of the apparatus and imaged images.

Figure 3A:
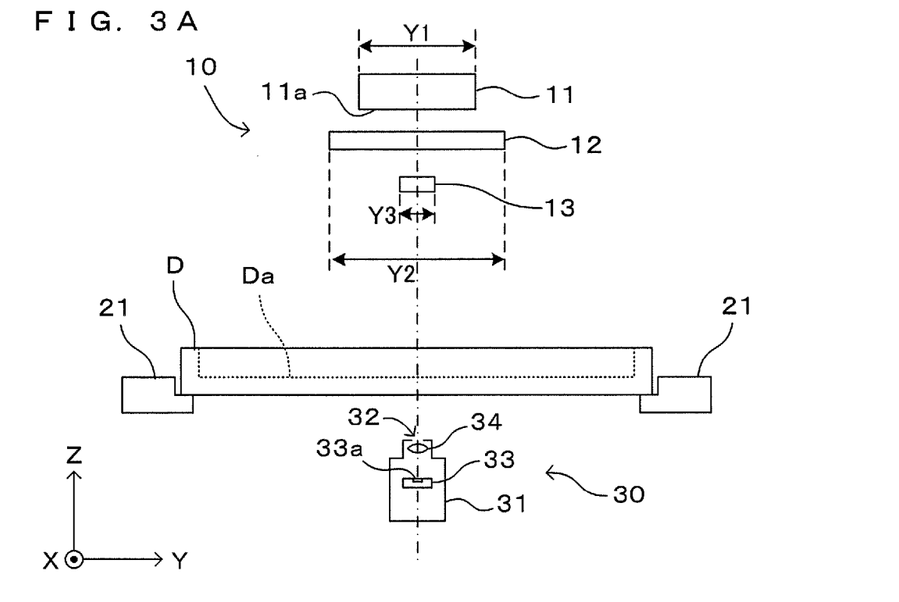
FIGS. 3A and 3B are side views showing the arrangement of a main configuration of the imaging apparatus.
Figure 3B:
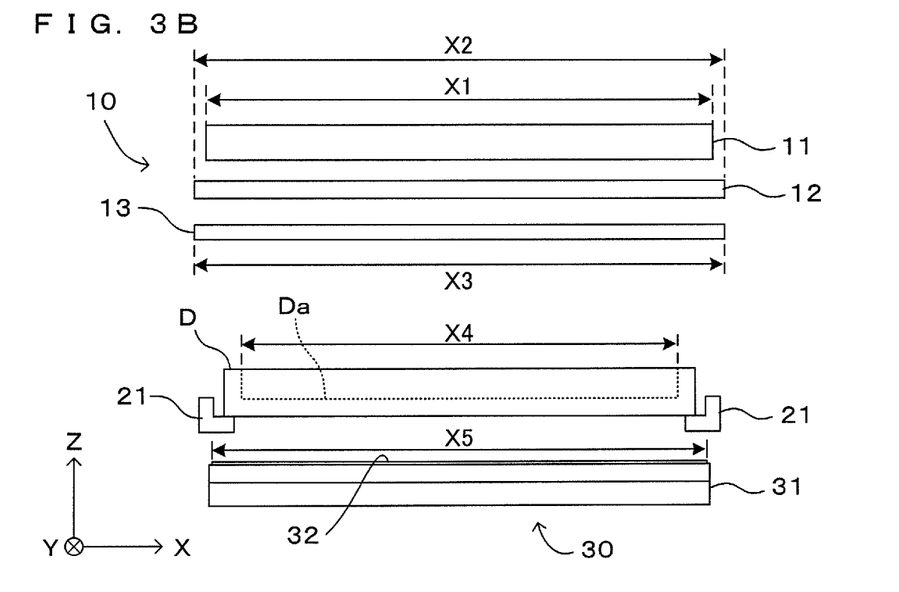

FIGS. 3A and 3B are side views showing the arrangement of a main configuration of this imaging apparatus. More specifically, FIG. 3A is a side view of a main part of this imaging apparatus viewed in the X direction. FIG. 3B is a side view of the main part of this imaging apparatus viewed in the Y direction. A dimensional relationship of each component is described with reference to these figures. As shown in FIG. 3A, a length Y2 of the diffusion plate 12 is longer than a length Y1 of the light source 11 (strictly, light emitting surface 11a) in the Y direction. Further, a length Y3 of the light shielding member 13 is shorter than the length Y1 of the light source 11. The length Y3 of this light shielding member 13 is preferably constant over a length range at least not shorter than an inner diameter X4 of the dish D in the X direction.

As shown in FIG. 3A, the imaging unit 30 includes a one-dimensional imaging device 33 having a light receiving surface 33a extending in the X direction and an imaging optical system 34 for imaging an image of an imaging object on the light receiving surface 33a in the housing 31. A device known as a so-called linear image sensor can be used as the one-dimensional imaging device 33. For example, a CCD line sensor, a CMOS line sensor or the like can be applied. A focus of the optical system 34 is adjusted to the inner bottom surface Da of the dish D held on the stage 21, i.e. the culture surface where a biological sample as the imaging object is cultured. The light receiving window 32 may have a function as a diaphragm for restricting a direction of light to be incident on the optical system 34.

A dashed-dotted line of FIG. 3A indicates an optical axis direction of the optical system 34. Note that a concept of an optical axis plane is applied instead of an optical axis if the optical system 34 is not rotationally symmetric and extends in the X direction like a cylindrical lens or a rod lens array. Although shown as a line in FIG. 3A, the optical axis plane of the optical system 34 coincides with an XZ plane and is perpendicular to the dish inner bottom surface Da. Each of the light emitting surface 11a of the light source 11, the diffusion plate 12, the light shielding member 13 and the light receiving window 32 of the imaging unit 30 arranged in this order from top at least partly intersects with the optical axis plane of the optical system 34.

As shown in FIG. 3B, a length X2 of the diffusion plate 12 is longer than a length X1 of the light source 11 (strictly, light emitting surface 11a) in the X direction. Further, a length X3 of the light shielding member 13 is at least longer than the length X1 of the light source 11, more preferably not shorter than the length X2 of the diffusion plate 12. Further, the length X2 of the diffusion plate 12 and the length X3 of the light shielding member 13 are longer than the inner diameter X4 of the dish D. More preferably, the length X1 of the light source 11 is also longer than the inner diameter X4 of the dish D.

A length X5 of the light receiving window 32 of the imaging unit 30 in the X direction is also longer than the inner diameter X4 of the dish D. This enables a two-dimensional image of the entire bottom surface of the dish D to be obtained by moving the imaging unit 30 to scan once relative to the dish D. Note that if the optical system 34 is a reduction optical system, it is not always necessary that a length of the one-dimensional imaging device 33 is not shorter than the inner diameter X4 of the dish D as long as a range not shorter than the inner diameter X4 of the dish D can be imaged in the X direction. Further, in the case of the imaging an image of the dish D in the form of band images divided in the X direction, an imaging unit of a size corresponding to that imaging range may be used.

Figure 4A:
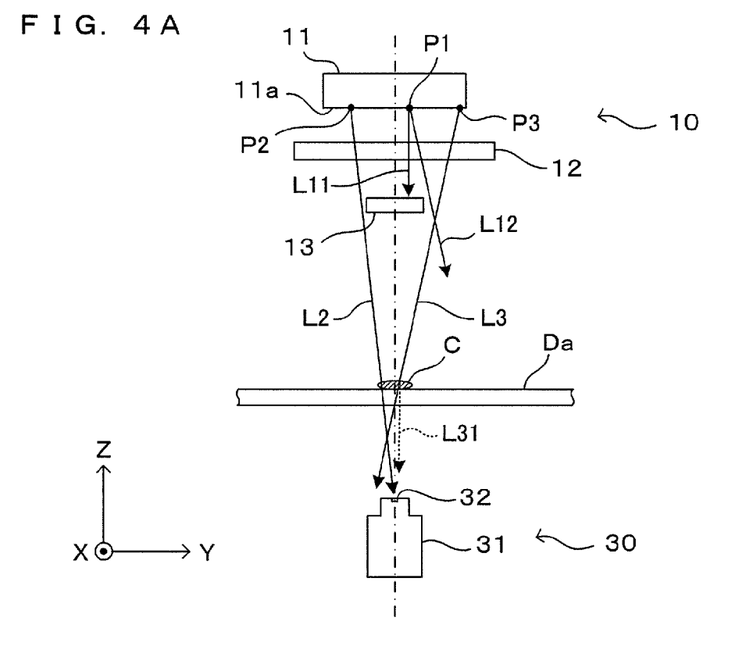
FIGS. 4A and 4B are views showing a state of incidence of illumination light on the imaging object in the imaging apparatus.
Figure 4B:
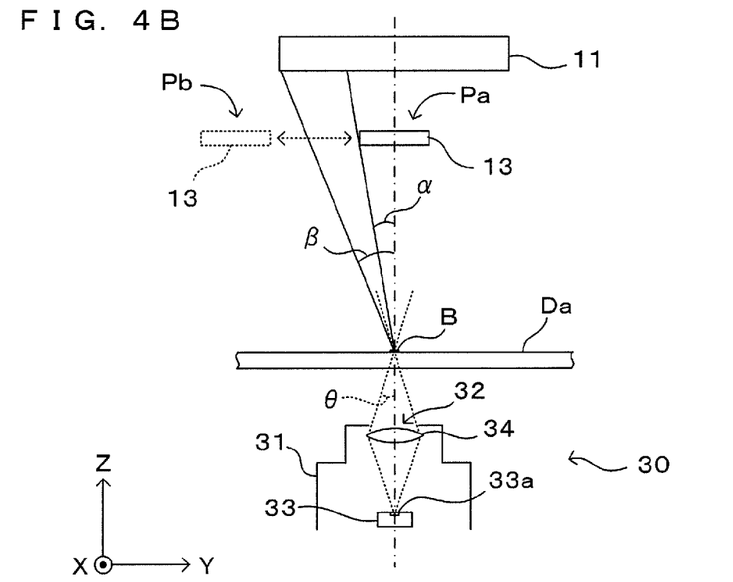

FIGS. 4A and 4B are views showing a state of incidence of illumination light on the imaging object in this imaging apparatus. More specifically, FIG. 4A is a view showing an example of an optical path of light emitted from several typical points of the light source 11, and FIG. 4B is a view showing a preferable range of an incident angle of the illumination light on the imaging object. As shown in FIG. 4A, light L11, L12 emitted from a point P1 close to the optical axis plane indicated by a dashed-dotted line has a propagation path thereof blocked by the light shielding member 13 or propagates in a direction to be separated from the optical axis. Thus, the light from the point P1 is not incident on an imaging object C, which is located near the optical axis plane and an object of one-dimensional imaging by the imaging unit 30, out of cells or the like adhering to the inner bottom surface Da of the dish D.

On the other hand, for points on the light emitting surface 11a distant from the optical axis plane, there are cases where, for example, light L2 emitted from a point P2 shown in FIG. 4A is incident on the imaging object C and transmits therethrough to reach the light receiving window 32 of the imaging unit 30. Further, light L3 emitted from a point P3 more distant from the optical axis plane and incident on and transmitted through the imaging object C is not directly incident on the imaging unit 30, but light L31 scattered in the imaging object C is incident on the light receiving window 30 of the imaging unit 30 in some cases.

As just described, in the imaging mode of this embodiment, a part of illumination light having an optical path to be incident on the light receiving window 32 of the imaging unit 30 through the imaging object C from the light source 11 is shielded by the light shielding member 13 and is not incident on the imaging object C. Particularly, light emitted from a position close to the optical axis plane and incident on the imaging object C from a direction approximate to a vertical direction is shielded by the light shielding member 13. On the other hand, light emitted from a position a little distant from the optical axis plane is incident on the imaging object C from an oblique direction without being shielded by the light shielding member 13.

Thus, as compared with the normal bright field imaging technology as disclosed in JP2013-072684A described above, transmitted light components transmitted through the imaging object C from the light source 11 and incident on the light receiving window 32 of the imaging unit 30 are reduced. However, bright field illumination light is not completely shielded, and a part of the light, more specifically the bright field illumination light from an oblique direction is allowed to be incident.

Further, for light from a more outward position to be incident on the imaging object C from a direction in which the transmitted light is not incident on the imaging unit 30, only scattered light components are incident on the light receiving window 32 of the imaging unit 30. Such incident light acts similarly to dark field illumination light in the dark field imaging technology.

That is, in this embodiment, imaging with a high image contrast is enabled as with the dark field imaging technology by allowing the illumination light to be incident on the imaging object C from the direction oblique to the optical axis plane and the imaging unit 30 to receive the scattered light components. On the other hand, since the light transmitted through the imaging object C from the light source 11 is allowed to be incident on the imaging unit 30 to a certain extent, a brighter image can be obtained and a problem of insufficient brightness in a dark field image can be solved.

If the light shielding member 13 is not provided and all the transmitted light components are allowed to be incident on the imaging unit 30, an image becomes brighter, but an improvement in image contrast cannot be desired due to weaker scattered light components. In this embodiment, it is possible to combine the brightness of an image and a high image contrast by allowing the scattered light components to be incident on the imaging unit 30 without being shielded while partly limiting the incidence of the transmitted light components on the imaging unit 30 by the light shielding member 13. A further improvement in image quality can be realized by optimizing an intensity ratio of the transmitted light components and the scattered light components.

A region located in an imaging range by the one-dimensional imaging device 33 provided in the imaging unit 30 out of the dish inner bottom surface Da on which an imaging object is to be carried is considered. As shown in FIG. 4B, this region can be expressed as a strip-like region B extending long in a longitudinal direction (X direction) of the one-dimensional imaging device 33 while having a microscopic length equivalent to a resolution of the one-dimensional imaging device 33 in a width direction (Y direction) perpendicular to the longitudinal direction. This strip-like region B is a partial surface area of the dish inner bottom surface Da imaged on the light receiving surface 33a of the one-dimensional imaging device 33 when the position of the imaging unit 30 is fixed with respect to the dish D. Although not clearly shown, the strip-like region B extends from one end to the other end of the dish inner bottom surface Da along the X direction.

A view angle when the light shielding member 13 is viewed from the strip-like region B in the YZ plane perpendicular to the longitudinal direction (X direction) of the strip-like region B is denoted by $\alpha$, and a viewing angle when the light emitting surface 11a is viewed from the strip-like region B is denoted by $\beta$. Note that although an angle up to one end part of an object based on the optical axis plane is defined as a viewing angle, an angle between opposite end parts of the object may be defined as a viewing angle as long as the same definition is used for a plurality of angles appearing in FIG. 4B. Particularly, if the light emitting surface 11a or the light shielding member 13 is asymmetrically shaped or arranged with respect to the optical axis plane, an angle at which the opposite ends of these members are viewed from the strip-like region B is preferably a viewing angle. Here, the above definition is used under the premise that these are symmetrically arranged with respect to the optical axis plane.

Here, if $\alpha=0$, a so-called bright field illumination condition is set. If $\alpha \geq \beta$, the illumination light from the light source 11 is not incident on the strip-like region B at all. According to the principle of illumination of this embodiment, $0<\alpha<\beta$. The viewing angle $\alpha$ at which the light shielding member 13 is viewed from the strip-like region B is more desirably located within the viewing angle $\beta$ at which the light emitting surface 11a is viewed from the strip-like region B. By setting so, light oblique to the optical axis plane can be incident on the strip-like region B from opposite sides in the Y direction. This enables optical characteristics of an imaging object in the strip-like region B, particularly a surface state thereof to be more precisely reflected on an image.

On the other hand, a viewing angle when the light receiving window 32 of the imaging unit 30 is viewed from the strip-like region B is denoted by $\theta$. Here, if $\theta \leq \alpha$, a so-called dark field illumination condition is set under which the transmitted light from the strip-like region B is not received by the imaging unit 30 at all. In this embodiment, $\theta>\alpha$. By setting so, transmitted light components to be incident from an oblique angle and received by the imaging unit 30 through the strip-like region B are created. These contribute the brightness of an image.

To make an image brighter, $\beta \geq \theta$ is preferable. By setting so, the brightness of the image can be maximized by allowing more light from the oblique direction to be incident on the imaging unit 30. If the viewing angle $\beta$ of the light emitting surface 11a is made even larger than the viewing angle $\theta$ of the light receiving window 32, it does not contribute to the brightness of the image very much since the quantity of the transmitted light incident on the imaging unit 30 is not increased. However, since the light quantity of the scattered light components can be increased, an image contrast can be further improved.

The entire dish inner bottom surface Da can be scanned to obtain a two-dimensional image thereof by performing imaging by the imaging unit 30 at each position while successively moving the strip-like region B in the Y direction by integrally moving the light source 11, the diffusion plate 12, the light shielding member 13 and the imaging unit 30 to scan in the Y direction relative to the imaging object. By performing this under illumination satisfying the above conditions, a two-dimensional image can be imaged with particularly good image quality by combining the brightness of the image and a high image contrast.

Note that, for example, in the case of imaging by an area image sensor, illumination satisfying the above conditions in the entire two-dimensional region to be simultaneously imaged is virtually impossible. Further, even in the case of using a linear image sensor, the same holds true for a configuration in which only the linear image sensor is moved to scan relative to an illumination light source and an imaging object. In this embodiment, since the imaging device 33 as a linear image sensor is used and the strip-like light shielding member 13 is arranged in parallel with the longitudinal direction of the imaging device 33, it is sufficient to consider the illumination condition only within a plane perpendicular to the longitudinal direction. By configuring the light source 11, the diffusion plate 12, the light shielding member 13 and the imaging device 33 to integrally move to scan relative to the imaging object, the entire imaging object can be imaged without changing a positional relationship of these, or with the above illumination condition maintained.

As described above, the light shielding member 13 is movable in the horizontal direction by the actuation of the light shielding member driving mechanism 413. Specifically, the light shielding member 13 is movable between a light shielding position Pa where the light is partly shielded on a propagation path of the light propagating from the light source 11 toward the strip-like region B as shown by solid line in FIG. 4B and a retracted position Pb which is laterally deviated from a propagation path of the light propagating from the light source 11 toward the light receiving window 32 of the imaging unit 30 and where the light is not shielded as shown by dotted line in FIG. 4B.

The dish D is imaged with the light shielding member 13 positioned at the light shielding position Pa. On the other hand, as described next, a shading correction processing is performed on the imaged image to prevent a reduction in image quality due to an emitted light quantity unevenness of the light source 11 and a sensitivity unevenness of the one-dimensional imaging device 33 in this embodiment. At the time of background imaging to obtain a shading characteristic for this, the light shielding member 13 is positioned at the retracted position Pb.

Figure 5:
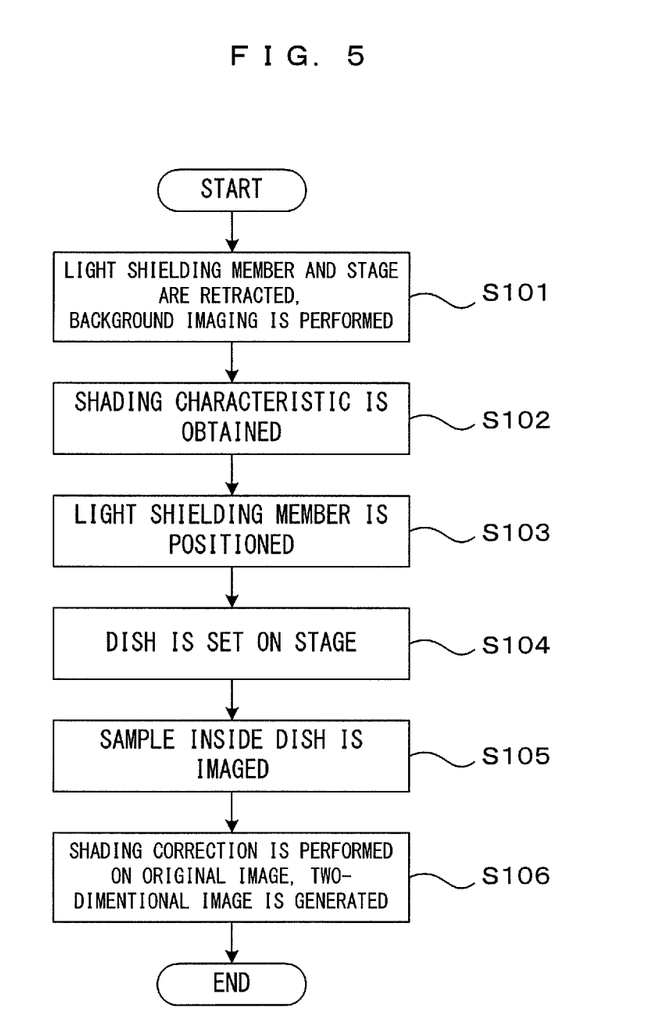
FIG. 5 is a flow chart showing an imaging operation in the imaging apparatus.

FIG. 5 is a flow chart showing an imaging operation in this imaging apparatus. This imaging operation is performed by the control unit 40 controlling each component of the apparatus to perform a predetermined operation based on a predetermined control program in response to a request from a user or an external apparatus via the input receiver 47.

First, the shading characteristic used in performing the shading correction is obtained. The light shielding member 13 and the stage 21 are retracted to such positions as not to shield light propagating from the light source 11 toward the imaging unit 30, and imaging by the imaging unit 30 is performed in this state (Step S101). A one-dimensional image imaged at this time is a background image reflecting only characteristics of the light source 11 and the imaging device 33. If there is an emitted light quantity unevenness of the light source 11 or a sensitivity unevenness of the one-dimensional imaging device 33, this appears as shade in a superimposed state. An image density at each position of the background image is stored as the shading characteristic in the storage 44 (Step S102). Since the imaging device 33 is for imaging a one-dimensional image and the relative positions of the light source 11 and the imaging unit 30 are constant, it is sufficient to obtain the background image and the shading characteristic only in one line in the X direction.

Subsequently, the light shielding member 13 is positioned at the light shielding position Pa (Step S103) and the dish D carrying an imaging object is set on the stage (Step S104). Note that the dish D may be set on the stage 21 before the background imaging is performed if it does not adversely affect a biological sample inside.

Imaging by the imaging unit 30 is successively performed while the dish D is moved in the Y direction together with the stage 21 by actuating the stage driving mechanism 421, whereby the dish inner bottom surface Da, particularly the biological sample carried thereon is imaged (Step S105). The image processor 430 performs the shading correction on original image data of an imaged one-dimensional image based on the previously obtained shading characteristic. Specifically, a pixel value adjustment necessary to cancel the shading characteristic is applied to each pixel of the imaged original image. Then, the image processor 430 synthesizes one-dimensional images in the X direction imaged at different positions in the Y direction to generate a two-dimensional image of the imaging object (Step S106). The generated image data is stored in the storage 44. The imaging operation is completed in the above manner.

Note that the shading correction is possible even if the shading characteristic based on the background image is obtained after the dish D is imaged. However, in a process of this embodiment to obtain a two-dimensional image by the scanning movement of the one-dimensional imaging device 33, the shading characteristic is preferably obtained before the dish D is imaged since a correction can be made every time for one-dimensional image data output every moment with the scanning movement.

Second Embodiment

Next, a second embodiment of the imaging apparatus according to this embodiment is described. In the imaging apparatus 1 of the above first embodiment, the light shielding member driving mechanism 413 is provided to move the light shielding member 13 between the light shielding position Pa and the retracted position Pb. Contrary to this, the imaging apparatus of the second embodiment described next enables a light shielding member to be positioned without providing a driving mechanism for moving the light shielding member.

Figure 6A:
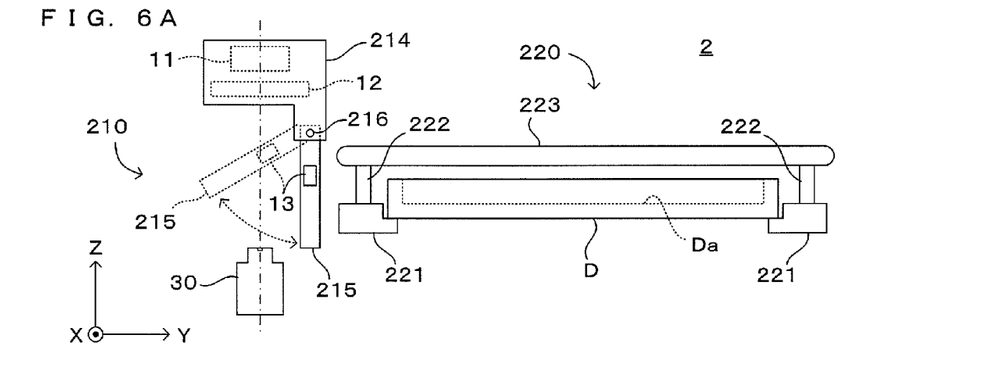
FIGS. 6A to 6C are views showing a main configuration of the second embodiment of the imaging apparatus according to the invention.
Figure 6B:
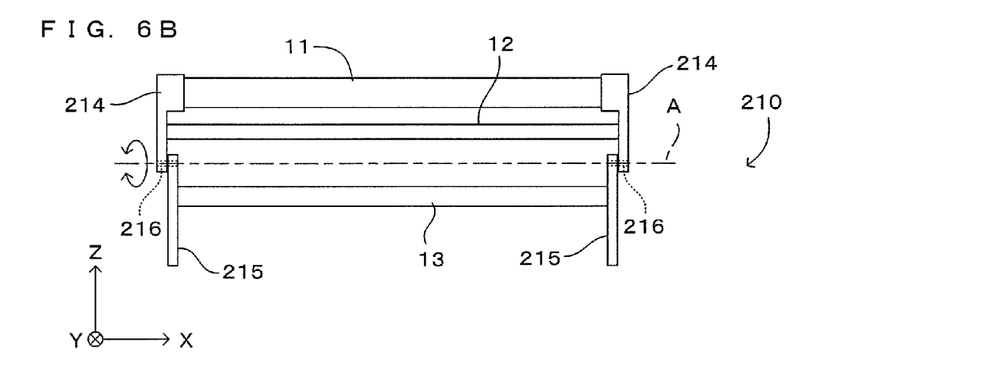
Figure 6C:
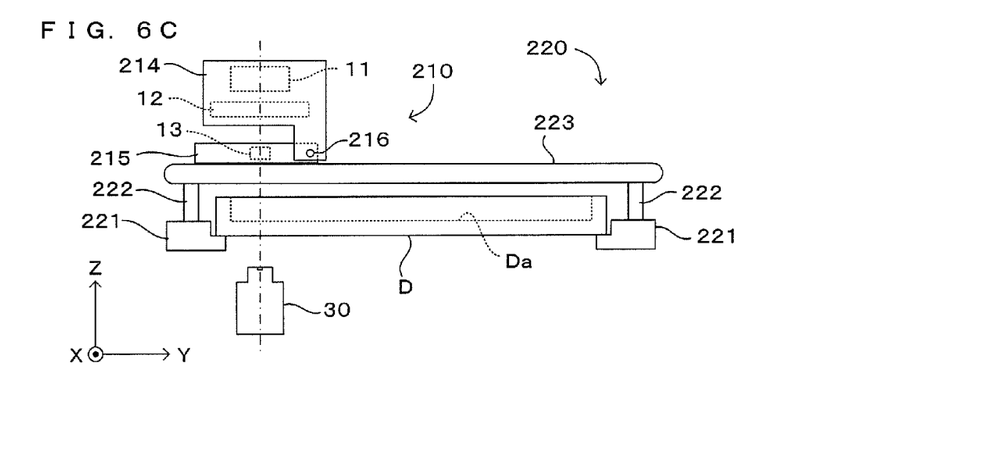

FIGS. 6A to 6C are views showing a main configuration of the second embodiment of the imaging apparatus according to this invention. Note that parts different from the imaging apparatus 1 of the first embodiment are mainly shown in FIGS. 6A to 6C. Each component provided in the first embodiment is similarly provided and similarly operates in this embodiment unless otherwise specified. Further, the components having the same functions as in the first embodiment are denoted by the same reference signs and not described.

FIGS. 6A and 6C are side views showing a main part of an imaging apparatus 2 of the second embodiment when viewed in the X direction. FIG. 6B is a side view showing the configuration of an illumination unit 210 of this embodiment when viewed in the Y direction. As shown in FIGS. 6A and 6B, opposite end parts of a light source 11 and a diffusion plate 12 in the X direction are supported by a pair of support frames 214 in the illumination unit 210 of the imaging apparatus 2 of the second embodiment. A pair of pivot arms 215 are rotatably attached to the support frames 214 via a pair of rotational support shafts 216. A light shielding member 13 extending in the X direction is mounted between the pair of pivot arms 215. When an assembly composed of the pair of pivot arms 215 and the light shielding member 13 is viewed in the Y direction, the assembly is substantially H-shaped as shown in FIG. 6B and integrally pivotable about a pivot axis A distant from an optical axis plane of an imaging unit 30 in the Y direction.

Further, a holding unit 220 of this embodiment includes a stage 221 configured similarly to the stage 21 of the first embodiment, a plurality of column members 222 standing in the Z direction on the upper surface of the stage 221 and a guide rail 223 supported on the column members 222 and extending in the Y direction.

In a state shown in FIG. 6A where the stage 221 is laterally retracted from a position between the illumination unit 210 and the imaging unit 30, the pivot arms 215 are hanging downward (−Z direction) by the action of gravity. Thus, the light shielding member 13 attached to the pivot arms 215 is located at a position below the rotational support shafts 216 and distant from the optical axis plane of the imaging unit 30 (retracted position). At this time, light propagating from the light source 11 toward the imaging unit 30 is not shielded by the light shielding member 13 and background imaging can be performed in this state.

On the other hand, when the stage 221 moves in the Y direction and the dish D enters between the illumination unit 210 and the imaging unit 30, an end surface of the guide rail 223 comes into contact with the pivot arms 215, whereby the tips of the pivot arms 215 move onto the guide rail 223 and the pivot arms 215 rotate about the axis A. Finally, as shown in FIG. 6C, the pivot arms 215 are pushed up to reach a substantially horizontal state, whereby the light shielding member 13 is positioned on the optical axis plane of the imaging unit 30 (light shielding position). In this state, an imaging object in the dish D is imaged while light propagating from the light source 11 toward the imaging unit 30 is partly shielded as in the first embodiment.

As just described, in the imaging apparatus 2 of the second embodiment, the light shielding member 13 can be moved between the retracted position and the light shielding position utilizing the movement of the stage 221 even if a mechanism for actively moving the light shielding member 13 is not provided.

Third Embodiment

Next, a third embodiment of the imaging apparatus according to this invention is described. An apparatus configuration of the third embodiment may be the same as that of the first or second embodiment. A feature of this embodiment is to optimize an illumination condition, i.e. to adjust the light quantity of the illumination unit before the imaging operation of FIG. 5 is performed.

Figure 7A:
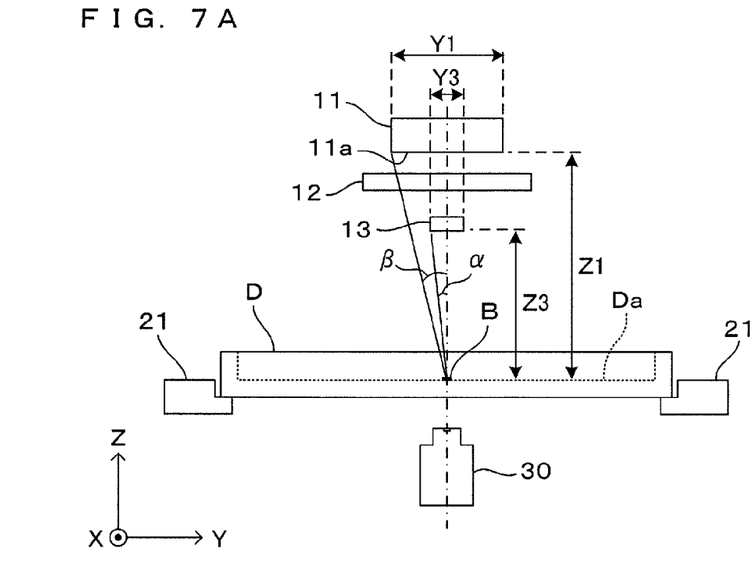
FIGS. 7A and 7B are drawings showing the principle of an illumination unit adjustment in the third embodiment.
Figure 7B:
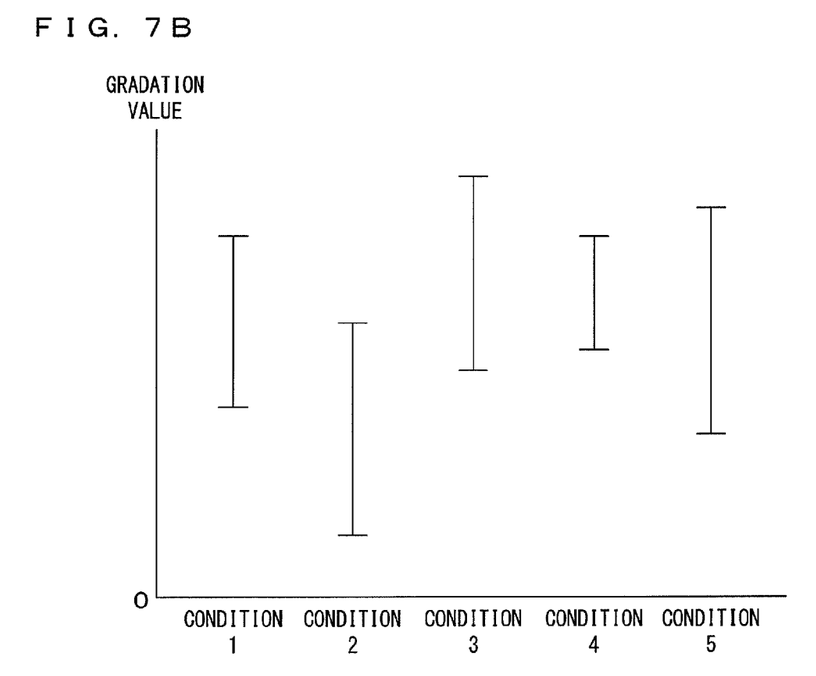

FIGS. 7A and 7B are drawings showing the principle of an illumination unit adjustment in the third embodiment. More specifically, FIG. 7A is a view showing factors affecting an illumination light quantity, and FIG. 7B is a graph illustrating a distributed state of gradation values when the same sample was imaged under various illumination conditions. As described above, in the embodiments of the imaging apparatus according to the invention, the ratio of the transmitted light components and the scattered light components to be incident on the imaging unit 30 changes according to the values of the viewing angle α when the light shielding member 13 is viewed from the strip-like region B imaged by the imaging unit 30 out of the inner bottom surface Da of the dish D carrying the imaging object and the viewing angle β when the lower surface (light emitting surface) 11a of the light source 11 is viewed from the strip-like region B. When that ratio is appropriate, it is possible to obtain an image with excellent image quality which has both the brightness of the image and a high image contrast.

As is clear from a relationship shown in FIG. 7A, a length Y1 of the light source 11 (light emitting surface 11a) in the Y direction, a length Y3 of the light shielding member 13 in the Y direction, a distance Z1 in the Z direction between the light source 11 (light emitting surface 11a) and the imaging object (dish inner bottom surface Da), a distance Z3 in the Z direction between the light shielding member 13 and the dish inner bottom surface Da and the like can be considered as factors for determining these viewing angles α, β. The ratio of the transmitted light components and the scattered light components can be adjusted by changing the viewing angles α, β using at least one of these as a control factor. For example, the following adjustment can be made.

First, a standard biological sample obtained by culturing cells or the like in the dish D or a dummy sample simulating that is prepared, and a two-dimensional image of the sample is imaged under each illumination condition while changing the illumination condition by differentiating a combination of the control factors described above. Then, gradation values for each pixel of the obtained two-dimensional original images are obtained, and a distribution range of the gradation values in each image is obtained. At this time, the gradation values of the pixels are more preferably statistically processed to eliminate the influence of pixels having extreme gradation values due to noise or the like. For example, a standard deviation σ in the distribution of the gradation values may be calculated and a range of 3σ may be set as a distribution range.

If imaging is performed under various illumination conditions, the distribution range of the gradation values in the imaged image under each condition can be obtained. As shown in FIG. 7B, because of a difference in the ratio of the transmitted light components and the scattered light components to be incident on the imaging unit 30 due to a difference in the illumination condition, the distribution range of the gradation values differs even for the same sample. Out of these, the illumination condition having a distribution range maximally wide and skewed toward a low gradation value side, i.e. a bright side may be selected as an optimal condition. More simply, the condition having a widest distribution range may be selected as the optimal condition and, if there are a plurality of conditions having comparable distribution ranges, the illumination condition whose distribution range is located most on the lower gradation value side may be selected.

For such a processing of optimizing the illumination condition, the above control factors may be made adjustable in a finished product of the imaging apparatus and the user may be able to perform this processing if necessary. For example, if the user can perform the processing of optimizing the illumination condition when judging it necessary to deal with a fact that the brightness and contrast of an image differ depending on the type of a medium or cells or the like cultured in the medium, it is convenient for the user.

Further, the apparatus may be shipped after the illumination condition is adjusted by an operator at the time of shipment, and the illumination condition may be fixed after shipment. Further, a plurality of illumination conditions may be preset and selectable according to a purpose. Furthermore, also for the purpose of determining the dimensions and arrangement of each component, for example, in the design stage of the apparatus, it is possible to apply the principle of optimization described above. These optimization processings are desirably performed at least before an actual sample is imaged.

Modifications

Figure 8A:
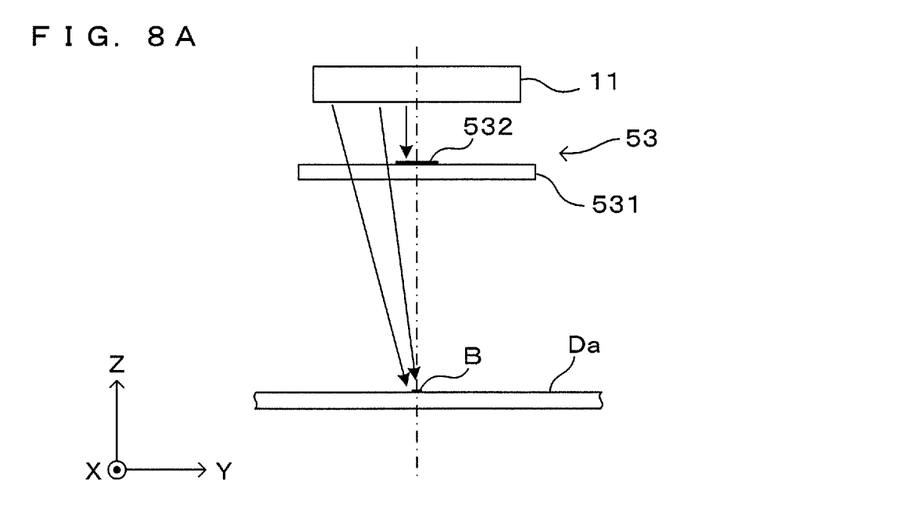
FIGS. 8A and 8B are views showing modifications of the light shielding member.
Figure 8B:
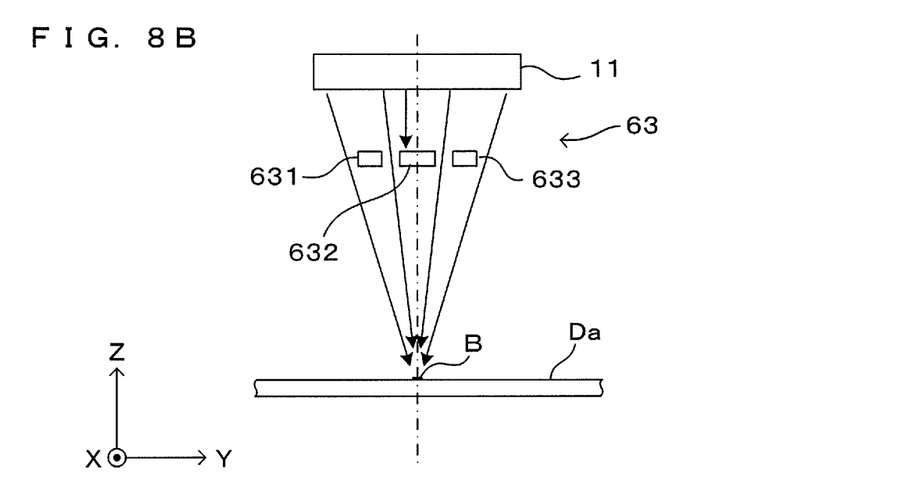
Figure 9:
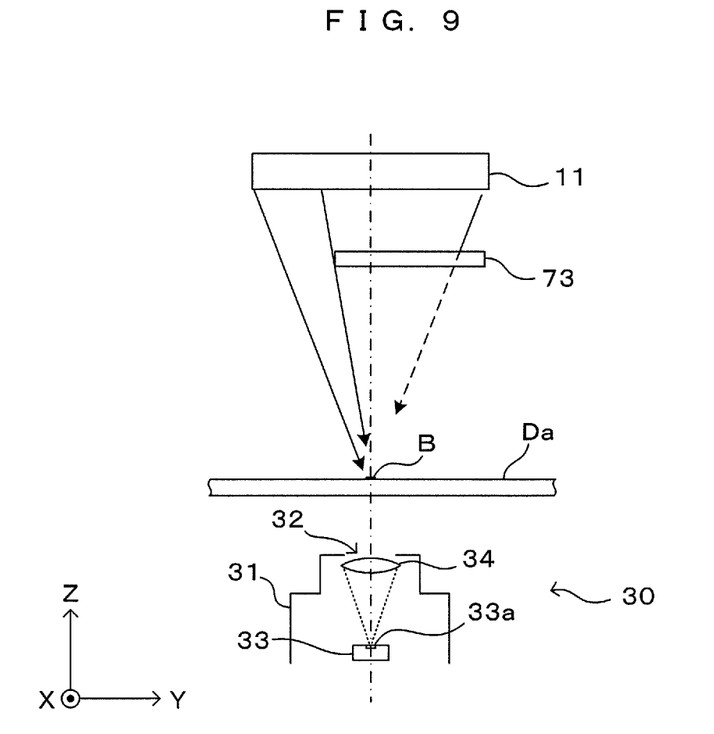
FIG. 9 is a view showing another modification of the light shielding member.

FIGS. 8A, 8B and 9 are views showing modifications of the light shielding member. A light shielding member 53 according to a first modification shown in FIG. 8A is such that a light shielding strip 532 formed of a light shielding material into a strip shape extending in the X direction is provided on one surface of a flat member 531 transparent to illumination light. The light shielding strip 532 can be formed by various forming methods such as application, bonding and deposition of the light shielding material to or on the flat member 531. Also by such a configuration, light propagating from the light source 11 toward the strip-like region B of the dish inner bottom surface Da can be partly shielded and can control the ratio of the transmitted light components and the scattered light components to be incident on the imaging unit as with the light shielding member 13 of the first embodiment. The flat member 531 may also have a function as a diffusion plate.

In a second modification shown in FIG. 8B, a light shielding member 63 is configured by a plurality of strip-like members (three strip-like members 631, 632 and 633 in this example) each extending in the X direction. In such a configuration, an incident direction and a light quantity of illumination light to be incident on the strip-like region B can be more finely adjusted by controlling a width of each strip-like member and gaps between them. Note that the width of each strip-like member needs not be equal. Further, a plurality of strip-like members may be formed on a transparent member by combining the second modification with the first modification described above.

In a third modification shown in FIG. 9, a light shielding member 73 extends long in the (+Y) direction as is clear in comparison to the first embodiment shown in FIG. 4A, and light emitted from the light source 11 at a (+Y) side of the optical axis of the optical system 34 is not incident on the strip-like region B. In an experiment conducted by the inventors of this application, such a configuration slightly lowers the brightness of an image as compared with the configuration of the first embodiment, but provides a good result in terms of an image contrast. Note that no significant difference is seen regardless of whether the light shielding member 73 extends toward the (+Y) side or toward a (−Y) side, i.e. extends toward an upstream side or a downstream side in a scanning direction of the imaging unit 30 relative to the dish D, and a similar imaging result is obtained regardless of in which direction the light shielding member 73 extends.

Miscellaneous

As described above, the imaging apparatus of first embodiment includes the stage 21 configured to hold the dish D carrying a biological sample as an imaging object on the flat inner bottom surface Da, the light source 11 configured to emit light toward the dish inner bottom surface Da from the light emitting surface 11a disposed to face the inner bottom surface Da of the dish D held on the stage 21, the imaging unit 30 including the strip-like light receiving window 32 provided along the X direction parallel to the dish inner bottom surface Da at a side of the dish inner bottom surface Da opposite to the light emitting surface 11a and configured to receive the light incident on the light receiving window 32 and image an image of the strip-like region B extending in the X direction out of the dish inner bottom surface Da, the strip-like light shielding member 13 extending in the direction parallel to the X direction between the light emitting surface 11a and the dish inner bottom surface Da and configured to shield a part of the light emitted from the light emitting surface 11a and propagating toward the strip-like region B, and the stage driving mechanism 421 configured to integrally and relatively move the light emitting surface 11a, the light receiving window 32 and the light shielding member 13 in the Y direction parallel to the dish inner bottom surface Da and intersecting with the X direction with respect to the dish D held on the stage 21, and images a two-dimensional image of the imaging object.

According to such a configuration, the ratio of the transmitted light components and the scattered light components to be received by the imaging unit 30 can be adjusted by controlling the incident direction and the light quantity of the illumination light to be incident on the strip-like region. Thus, an image with good image quality can be obtained by combining the brightness of the image obtained by the transmitted light components and a high image contrast obtained by the scattered light components.

Further, in the above embodiments, the viewing angle $\beta$ at which the light emitting surface 11a is viewed from the strip-like region B is larger than the viewing angle $\alpha$ at which the light shielding member 13 is viewed from the strip-like region B in the YZ plane intersecting with the strip-like region B and perpendicular to the X direction. Thus, at least a part of the light emitted from the light emitting surface 11a can be reliably incident on the strip-like region B without being shielded by the light shielding member 13. This increases the intensity of the light received by the imaging unit 30 and improves the brightness of the image and the image contrast. Further, by setting the viewing angle $\alpha$ to be located within the viewing angle $\beta$, the illumination light can be incident on the imaging object from both directions and a surface state of the imaging object can be particularly satisfactorily reflected on the image.

Further, in the above embodiments, in the YZ plane intersecting with the strip-like region B and perpendicular to the X direction, the viewing angle $\theta$ at which the light receiving window 32 is viewed from the strip-like region B is larger than the viewing angle $\alpha$. According to such a configuration, the light incident on the strip-like region B from the light emitting surface 11a and transmitted through the region B is incident on the light receiving window 32, wherefore the brightness of the image can be reliably increased.

Further, in the above embodiments, a perpendicular of the dish inner bottom surface Da including the strip-like region B intersects with the light shielding member 13. In other words, the optical axis plane of the imaging unit 30 passing through the strip-like region B is in a positional relationship to cross the light shielding member 13. Thus, a reduction in image contrast can be prevented by reliably shielding light to be incident on the strip-like region B from a direction approximate to the vertical direction by the light shielding member 13. On the other hand, the brightness of the image and the image contrast can be ensured by allowing oblique light incidence on the strip-like region B to a certain extent.

Further, in the above embodiments, the length Y3 of the light shielding member 13 along the Y direction is shorter than the length Y1 of the light emitting surface 11a along the Y direction. Thus, light emitted from the light emitting surface 11a is not completely shielded by the light shielding member 13. Furthermore, the length Y3 of the light shielding member 13 along the Y direction is constant in the X direction over a length not shorter than the length X1 of the light emitting surface 11a along the X direction. This enables the strip-like region B to be illuminated under a uniform illumination condition in the X direction and enables the image quality to be uniformized. If the illumination condition is set on one YZ plane, the same illumination condition is guaranteed in the entire dish inner bottom surface Da.

Further, in the above embodiments, the light shielding member 13 is movable between the light shielding position Pa where the light propagating from the light emitting surface 11a toward the dish D (more specifically, strip-like region B thereof) between the dish D and the light emitting surface 11a is partly shielded and the retracted position Pb where the light is not shielded. The image processor 430 is provided as a shading corrector for performing a shading correction on an original image obtained by imaging the imaging object in a state where the light shielding member 13 is located at the light shielding position Pa based on a background image imaged in the absence of dish D between the light emitting surface 11a and the imaging unit 30. By performing the shading correction in this way, a variation in image density due to an emitted light quantity unevenness of the light source 11 and a sensitivity unevenness of the one-dimensional imaging device 33 can be compensated and the deterioration of the image quality can be prevented.

Further, in the third embodiment, the illumination condition optimization processing of adjusting the quantity of light to be incident on the dish D is performed, using at least one control factor out of the size of the light emitting surface 11a, the size of the light shielding member 13, the distance Z3 between the light shielding member 13 and the dish D and the distance Z1 between the light emitting surface 11a and the dish D before the imaging object is imaged. More specifically, by controlling these control factors, the direction and light quantity of the light to be incident on the strip-like region B are adjusted to adjust a balance between the transmitted light components and the scattered light components emerging from the strip-like region B. According to such a configuration, imaging can be performed under an optimal illumination condition and the image quality can be optimized without dependence on changes of apparatus characteristics with the passage of time and differences in optical characteristics of imaging objects.

As described above, in the above embodiments, the dish D for carrying a biological sample such as cells as an imaging object corresponds to a "sample container" of the invention, and the inner bottom surface Da thereof corresponds to a "carrying surface" of the invention. The stages 21, 221 function as a "holder" of the invention, and the stage driving mechanism 421 functions as a "mover" of the invention.

Further, the light source 11 functions as an "illuminator" of the invention, and the light emitting surface 11a corresponds a "light emitting part" of the invention. Further, the imaging unit 30 functions as an "imager" of the invention, and the light receiving window 32 functions as a "light receiving part" of the invention. Further, the light shielding member 13 functions as a "light shield" of the invention, and the image processor 430 functions as a "shading corrector" of the invention.

Further, in the above embodiments, the X direction and the Y direction respectively correspond to a "first direction" and a "second direction" of the invention. Further, the viewing angles α, β and θ respectively correspond to a "first viewing angle", a "second viewing angle" and a "third viewing angle".

Further, in the imaging operation of the above embodiment, Steps S103 and S104 together correspond to a "first step" of the invention. Further, Steps S105 and S106 respectively correspond to a "second step" and a "fourth step" of the invention. Further, Steps S101 and S102 together correspond to a "third step" of the invention. The illumination condition optimization processing whose principle is shown in FIG. 7 corresponds to a "fifth step" of the invention.

Note that the invention is not limited to the above embodiments and various changes other than the above ones can be made without departing from the gist thereof. For example, in the imaging apparatuses of the above embodiments, the dish D carrying a biological sample as an imaging object is held in a substantially horizontal posture and imaging is performed by allowing illumination light to be incident from above and receiving the light emerging downward. However, the posture and the positional relationship are not limited to these. For example, similar effects can be obtained by setting the illumination condition and performing imaging as described above also in a configuration for allowing illumination light to be incident on an imaging object from below and receiving the light emerging upward.

Further, in the above embodiments, the illumination unit 10 and the imaging unit 30 are fixed and the scanning movement of the imaging unit 30 is realized by moving the stage 21 holding the dish D. Conversely, even if the dish D is fixed and the illumination unit 10 and the imaging unit 30 are moved, it is technically equivalent. In such a case, the influence of the vibration of the dish D during the imaging on the sample can be reduced.

Further, although the imaging device 33 and the optical system 34 are proximately disposed in the same housing 31 in the above embodiments, incident light may be finally guided to an image sensor while the direction thereof is changed by a prism, a mirror or the like as in an optical system used, for example, in a flat bed type document scanner. In this case, it is sufficient to move a part of the optical system to scan an imaging object and it is not essential to move the image sensor itself relative to the imaging object.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging apparatus for imaging a two-dimensional image of an imaging object, comprising:

a holder which holds a sample container carrying a biological sample as the imaging object on a carrying surface;

an illuminator which emits light from a light emitting part facing the carrying surface of the sample container held by the holder toward the carrying surface;

an imager which includes a strip-like light receiving part provided at a side of the carrying surface opposite to the light emitting part and along a first direction parallel to the carrying surface, receives the light incident on the light receiving part and images an image of a strip-like region along the first direction out of the carrying surface;

a strip-like light shield which extends in a direction parallel to the first direction between the light emitting part and the carrying surface and shields a part of light emitted from the light emitting part toward the strip-like region; and a mover which integrally and relatively moves the light emitting part, the light receiving part and the light shield in a second direction parallel to the carrying surface and intersecting with the first direction with respect to the sample container held by the holder.

2. The imaging apparatus according to claim 1, wherein a first viewing angle at which the light shield is viewed from the strip-like region in a virtual plane intersecting with the strip-like region and perpendicular to the first direction is smaller than a second viewing angle at which the light emitting part is viewed from the strip-like region in the virtual plane, and the first viewing angle is involved within the second viewing angle.

3. The imaging apparatus according to claim 2, wherein a third viewing angle at which the light receiving part is viewed from the strip-like region in the virtual plane is larger than the first viewing angle.

4. The imaging apparatus according to claim 1, wherein a perpendicular of the carrying surface passing through an arbitrary point in the strip-like region intersects with the light shield.

5. The imaging apparatus according to claim 1, wherein a dimension of the light shield along the second direction is shorter than a dimension of the light emitting part along the second direction and constant in the first direction over a length not shorter than a dimension of the light emitting part along the first direction.

6. The imaging apparatus according to claim 1, wherein:
the light shield moves between a light shielding position between the sample container and the light emitting part at where light propagating from the light emitting part toward the sample container is partly shielded and a retracted position where the light is not shielded; and
the imaging apparatus further comprises a shading corrector for performing a shading correction on an image obtained by imaging the imaging object with the light shield located at the light shielding position based on an image imaged in the absence of the sample container between the light emitting part and the imager with the light shield located at the retracted position.

7. An imaging method, comprising:
a first step of arranging a light emitting part to face a carrying surface of a sample container carrying a biological sample as an imaging object on the carrying surface, arranging a light shield configured to shield a part of light emitted from the light emitting part and propagating toward the carrying surface between the light emitting part and the carrying surface, and arranging a light receiving part of an imager configured to image an image of a strip-like region along a first direction parallel to the carrying surface out of the carrying surface at a side of the carrying surface opposite to the light emitting part; and
a second step of imaging a two-dimensional image of the imaging object by integrally and relatively moving the light emitting part, the light receiving part and the light shield in a second direction intersecting with the first direction with respect to the sample container, wherein
the light shield is a strip-like member which extends in the first direction between the light emitting part and the carrying surface.

8. The imaging method according to claim 7, further comprising:
a third step of performing imaging by the imager in a state where the light shield and the sample container are not arranged between the light emitting part and the light receiving part; and
a fourth step of performing a shading correction on the image imaged in the second step based on an image imaged in the third step.

9. The imaging method according to claim 7, further comprising a fifth step of adjusting quantity of light to be incident on the sample container by controlling at least one of a size of the light emitting part, a size of the light shield, a distance between the light shield and the sample container and a distance between the light emitting part and the sample container in advance of the second step.

* * * * *